United States Patent [19]
Ogura et al.

[11] Patent Number: 5,892,133
[45] Date of Patent: Apr. 6, 1999

[54] REPELLENT AGENT AGAINST HARMFUL INSECTS AND PERFUME COMPOSITION CONTAINING THE SAME

[75] Inventors: Miharu Ogura; Akira Amano, both of Hiratsuka; Takeshi Yamamoto, Tokyo; Hideyuki Ohta, Hiratsuka, all of Japan

[73] Assignee: Takasago International Corporation, Tokyo, Japan

[21] Appl. No.: 898,070

[22] Filed: Jul. 22, 1997

[30] Foreign Application Priority Data

Jul. 24, 1996 [JP] Japan ..................................... 8-224302

[51] Int. Cl.$^6$ ..................................................... C07C 35/08
[52] U.S. Cl. .......................... 568/832; 568/834; 514/729; 514/819; 424/405
[58] Field of Search ............................. 424/405; 514/729, 514/819; 568/822, 829, 834, 832

[56] References Cited

U.S. PATENT DOCUMENTS 3,277,206 10/1966 Bain ........................................ 568/829
5,104,851 4/1992 Fujikura et al. ........................... 512/14

FOREIGN PATENT DOCUMENTS 39-19627 11/1964 Japan .
405170683 7/1993 Japan .

OTHER PUBLICATIONS

Total Synthesis of P–Menthenolides Bal et al Heterocycles 16(12) 2091–104, 1981.
An Unusal Compound–Koesel et al Prog. Essent. Oil Res. Proc Int. Symp. Essent. Oils., 16th, 1986.
Leffingwell et al Synthesis of Laevo Menthol from a By–Product R.J. Reynolds, 1973.

*Primary Examiner*—Neil S. Levy
*Attorney, Agent, or Firm*—Kubovcik & Kubovcik

[57] ABSTRACT

A repellent agent containing a 3-substituted p-menthane (or p-menthene) derivative represented by the following formula (1) is disclosed:

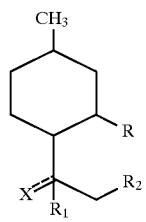

In the formula, R is a hydroxy group or hydroxyethyl group; $R_2$ is a hydrogen atom, hydroxy group, hydroxymethyl group, or alkoxy group having 1 to 3 carbon atoms; the double line is a double bond or a single bond, wherein $R_1$ is absent when the double line is a double bond, and $R_1$ is a hydrogen atom or hydroxy group when the double line is a single bond; provided that, when the double line is a single bond and $R_2$ is a hydrogen atom, both of R and $R_1$ are not a hydroxy group at the same time; and X is $CH_2$ when the double line is a double bond and is $CH_3$ when the double line is a single bond.

2 Claims, No Drawings

REPELLENT AGENT AGAINST HARMFUL INSECTS AND PERFUME COMPOSITION CONTAINING THE SAME

BACKGROUND OF THE INVENTION

1. Field of the Invention

The present invention relates to a repellent agent effective against hematophagous or biting insects such as mosquitoes, horseflies, fleas, ticks, lice, and the like. The present invention also relates to a perfume composition containing the repellent agent.

2. Description of the Related Art

Many diseases are known which are mediated by pests, particularly insects, and in particular diseases caused by hematophagous insects have become a serious problem.

For example, mosquitoes carry malaria, yellow fever, dengue fever, filariasis, or the like; fleas carry pest or the like; and chiggers carry trombiculiasis or the like. Most of these harmful living things play a role specific to the propagation of a pathogen such as viruses, rickettsia, bacteria, or the like.

Specifically, hematophagous insects and ticks which have sucked the blood of an animal having a disease and which carry a pathogenic organism therein next suck the blood of other persons, livestock, and pets, and thereby infect them with the pathogenic organism. Their infectious power is immeasurable.

When blood is sucked by a hematophagous insect, unpleasantness such as itching, rash, dermatitis, or the like occurs at the site where the blood is sucked.

Thus, the damage induced by such hematophagous insects is immense, and various methods of using repellents for controlling them are known.

A number of effective components for repellents against harmful insects have heretofore been developed and provided. Examples of the commercially available repellents are N,N-diethyl-m-toluamide, dialkyl phthalate, and the like, but none of them shows a sufficient repellent effect.

In particular, there is a problem with respect to duration of the repellent effect.

In order to solve this problem, there are disclosed as effective components for repellent agents against harmful insects, p-menthan-3,8-diol and derivatives thereof (Japanese Patent Application Publication (kokoku) No. 3-80138), p-menthan-1,2-diol, caren-3,4-diol, pinen-2,3-diol (U.S. Pat. No. 5,130,136), and the like.

Further, in order to improve the duration of the repellent effect there are disclosed a method of adding p-menthan-3,8-diol to a known effective component for repellent agents, N,N-diethyl-m-toluamide (Japanese Patent Application Laid-Open No. 3-133906), a method of microcapsulating p-menthan-3,8-diol (Japanese Patent Application Laid-Open No. 3-176404), and a method of supporting p-menthan-3,8-diol on an ethylene-vinyl acetate copolymer (Japanese Patent Application Laid-Open No. 2-191201).

However, attempts to make the repellent effect of these repellent agents last longer have not been sufficient, and there is still room for improvement.

When a spray-type composition containing a repellent agent is used, a remarkable effect can be attained immediately after spraying, but the effect lasts only for a short period of time. It is necessary to spray repeatedly many times to expect a long-term effect.

A new repellent agent is desired which maintains an excellent repellent effect over a long period of time so that repeated spraying becomes unnecessary.

SUMMARY OF THE INVENTION

Accordingly, an object of the present invention is to develop and provide a repellent agent containing a novel compound for repelling harmful insects which produces a long lasting excellent repelling effect.

Furthermore, another object of the present invention is to provide a perfume composition comprising the repellent agent.

The present inventors eagerly conducted studies in order to solve the above-mentioned problems.

Accordingly, the present invention provides (i) a repellent agent against harmful insects containing a 3-substituted p-menthane or p-menthene represented by the following formula:

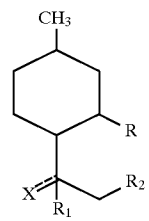

wherein, R is a hydroxy group or hydroxyethyl group; $R_2$ is a hydrogen atom, hydroxy group, hydroxymethyl group, or an alkoxy group having 1 to 3 carbon atoms; a double line consisting of a dotted line and a solid line (hereinafter referred to as "double line") is a double bond or a single bond, wherein $R_1$ is absent when the double line is a double bond, and $R_1$ is hydrogen atom or hydroxy group when the double line is a single bond, provided that, when the double line is a single bond and $R_2$ is a hydrogen atom, both of R and $R_1$ are not a hydroxy group at the same time; and X is $CH_2$ when the double line is a double bond and is $CH_3$ when the double line is a single bond; and (ii) a perfume composition comprising the repellent agent.

PREFERRED EMBODIMENTS OF THE INVENTION

The present invention is explained in detail hereinafter.

The repellent agent according to the present invention contains a compound represented by the following formula:

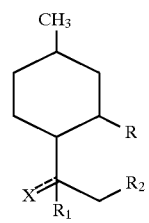

wherein R, $R_1$, double line, $R_2$ and X are as defined above.

Examples of the alkoxy group having 1 to 3 carbon atoms ($R_2$) include a methoxy group, ethoxy group, propoxy group, and isopropoxy group, and particularly the methoxy group and ethoxy group are preferred.

Among these compounds, the following compounds are more preferable.

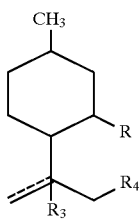

wherein R is a hydroxy group or hydroxyethyl group; $R_4$ is a hydrogen atom, hydroxy group, hydroxymethyl group, or an alkoxy group having 1 to 3 carbon atoms; a double line is a double bond or a single bond, wherein $R_3$ is a hydrogen atom or hydroxy group when the double line is a single bond, provided that, when R is hydroxyethyl, $R_3$ is a hydroxy group and $R_4$ is a hydrogen atom; when R is a hydroxy group and $R_3$ is absent (namely the double line is a double bond), $R_4$ is a hydroxy group; when R is a hydroxy group and $R_3$ is a hydroxy group, $R_4$ is a hydroxy group, methoxy group or ethoxy group; when R is a hydroxy group and $R_3$ is a hydrogen atom, $R_4$ is a hydroxymethyl group; X is $CH_2$ when the double line is a double bond and is $CH_3$ when the double line is a single bond.

These compounds can be easily prepared by utilizing known methods. Methods of preparing representative compounds are explained hereinafter.

In the following description the formulas for the compounds are presumed to have a $CH_3$ group in the 1-position and a $CH_2$ or $CH_3$ group in the 8-position (corresponding to the double line).

First, p-menth-8-ene-3,9-diol (1) is easily prepared by subjecting isopulegol to epoxidation, followed by isomerization with lithium diisopropylamide, according to the method disclosed in PCT/EP93/03164 (Equation A).

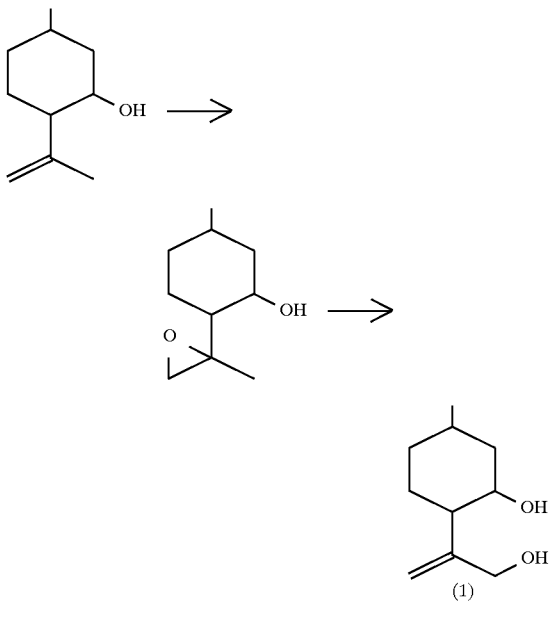

Moreover, p-menthan-3,9-diol obtained by hydrogenating the compound (1) has a repellent effect and can be used as a repellent.

A novel compound, 9-hydroxymethyl-p-menthan-3-ol (2) can be prepared by subjecting isopulegol to carbonylation and reducing the resulting bicyclolactone with a reducing agent obtained by combining lithium aluminum hydride, sodium borohydride, or the like with calcium chloride or the like, according to the method described in J. Organometallic Chem., Vol. 480, 1994, p. 91–102, which is shown in Equation B.

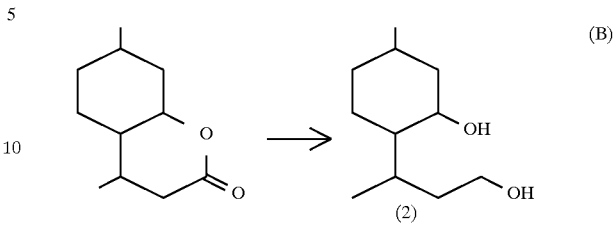

A novel compound, 3-(2-hydroxyethyl)-p-menthan-8-ol (3) can be similarly prepared by reducing chemically bicyclolactone which can be easily synthesized from citronellal and a malonic acid ester according the method described in Synthesis, 359, 1988 (see Equation C).

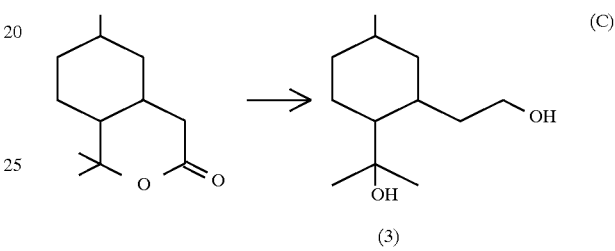

p-Menthan-3,8,9-triol (4) can be easily prepared by oxidizing isopulegol with osmium tetraoxide according to the method as described in M. Koepsel et al., Progress in Essential Oil Research, 1986 Walter de Gruyter & Co., Berlin-New York-Printed in Germany, p. 241–248, as shown in Equation D, and can also be easily prepared by hydrating an epoxide of isopulegol with an acid catalyst such as sulfuric acid or the like.

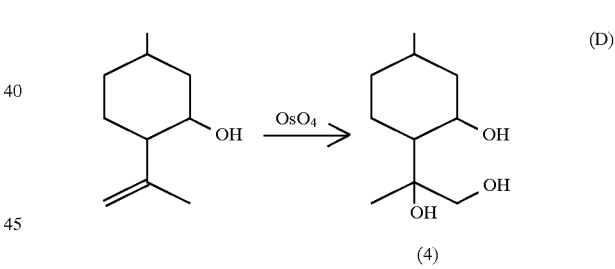

Further, 9-methoxy-p-menthan-3,8-diol (5) can be prepared by reacting an epoxide of isopulegol with methanol in the presence of a basic catalyst such as sodium methylate or the like, as shown in Equation E.

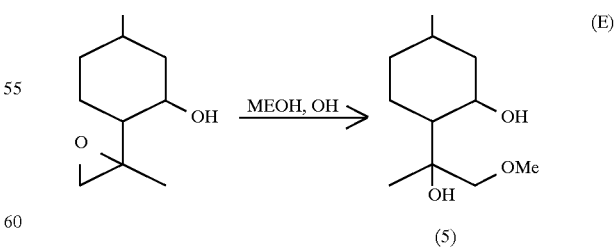

Alternatively, an epoxide of isopulegol may be reacted in the presence of a basic catalyst such as sodium methylate or the like in an alcohol such as ethanol, propanol, or the like; a polyhydric alcohol such as ethylene glycol, diethylene glycol, propylene glycol, glycerin, or the like; or cellosolve such as methyl cellosolve or the like, instead of methanol.

Since the above-mentioned compounds have 3 or 4 asymmetric carbon atoms, 8 or 16 stereoisomers including optical isomers are present. In the case of using the compounds as a repellent against harmful insects, an isomer can be used alone or in a combination of two or more thereof. Further, a mixture of isomers can be used without isolating procedures.

In the compound (2) having three asymmetric carbon atoms, for example, there are eight kinds of optical isomers as shown in the table below. That is, four kinds of geometric isomers (normal, neo, iso, and neoiso isomers) are present, and each has two kinds of enantiomers, which makes eight isomers in total.

The four 4S isomers in the upper row of the table are prepared from (3S)-(-)-citronellal, and the four 4R isomers in the lower row are prepared from (3R)-(+)-citronellal.

Further, (3S)-(-)-citronellal and (3R)-(+)-citronellal can be easily prepared from myrcene as a starting material, according to the method disclosed in Japanese Patent Application Laid-Open Nos. 58-4748 and 61-27949.

Similarly, with regard to the compounds (1), (3), (4), (5), and the like which can be produced from isopulegol as a starting material, all the optical isomers can be prepared from optical isomers of isopulegol.

Examples of a liquid diluent useful as a carrier are aromatic hydrocarbons such as toluene, xylene, tetralin, methylnaphthalene, and the like; alcohols such as isopropanol, cetyl alcohol, and the like; polyhydric alcohols such as propylene glycol, glycerin, and the like; cellosolves such as ethyl cellosolve and the like; fractions of distilled petroleum such as liquid paraffin and the like; esters such as dodecyl acetate and the like; ketones such as 2,6-hexadione and the like; ethers such as dibutyl ether and the like; animal and vegetable oils, fatty acids, and their esters; water; and the like. Examples of the solid diluent are clay, kaolin, talc, silica gel, calcium carbonate, montmorillonite, alumina, diatomaceous earth, and the like.

Examples of the surfactant are cationic surfactants, anionic surfactants, nonionic surfactants, amphoteric surfactants such as stearyl trimethyl ammonium chloride, sodium ligninsulfonate, ammonium polyoxyethylene alkylbenzene sulfonate, polyoxyethylene alkylphenyl ether, polyoxyethylene alkyl ether, laurylbetain, and the like.

In addition, carboxymethyl cellulose, polyvinyl alcohol, polyethylene glycol, sodium polyacrylate, gum arabic, gum xantanic, or the like can be used.

The repellent agent according to the present invention, for example, can be directly used by itself or mixed in a solvent

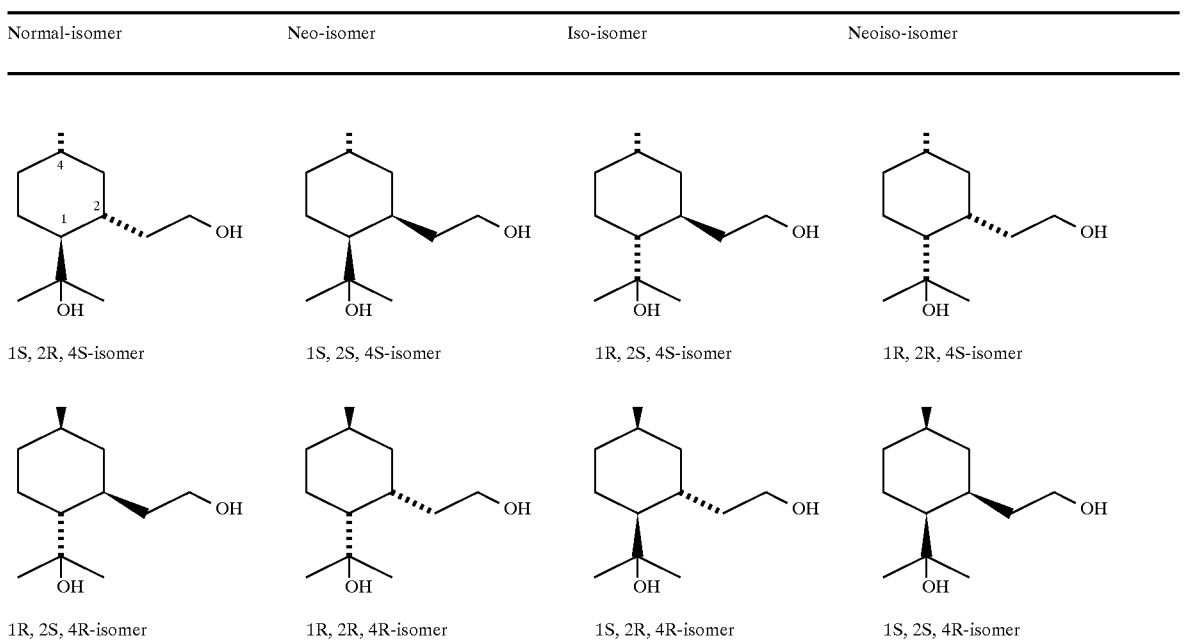

| Normal-isomer | Neo-isomer | Iso-isomer | Neoiso-isomer |

1S, 2R, 4S-isomer 1S, 2S, 4S-isomer 1R, 2S, 4S-isomer 1R, 2R, 4S-isomer 1R, 2S, 4R-isomer 1R, 2R, 4R-isomer 1S, 2R, 4R-isomer 1S, 2S, 4R-isomer In the present invention, the above-mentioned repellent compounds can be used alone or in combination of two or more thereof. There is no particular limitation in selecting the compounds to be combined when two or more thereof are used in combination.

The repellent agent against harmful insects of the present invention (hereinafter referred to as "repellent") can be prepared by mixing the repellent compound with other components such as various solvents and traditional adjuvants. However, the repellent agent according to the present invention can be used alone depending upon the purpose of the use or the site on which it is to be applied.

The method of preparing the repellent agent of the present invention is not specifically limited, and known methods can be employed.

The adjuvants include carriers (liquid diluents or solid diluents) and various surfactants.

such as water, alcohol, or the like for directly applying to the region where the repellent action against harmful insects is required. Further, the repellent agent according to the present invention can be preferably used in various forms suitable for application such as, for example, a cream, lotion, aerosol, emulsion, soap, body shampoo, shampoo, an interior perfume (or deodorant), or the like.

For example, in the case of human beings, it is sufficient to only apply to exposed skin cream or lotion containing the repellent agent, or to only apply the repellant agent by spraying.

The repellent agent against harmful insects according to the present invention can take the form in which a repellent compound or a repellent agent is carried on carriers such as inorganic porous materials, organic porous materials, resins, and the like.

Furthermore, the repellent agent according to the present invention can also take a known form, for example, a form in which a repellent compound or a repellent agent is carried within microcapsules.

For example, the repellent compound or the repellent agent according to the present invention can be carried on carriers consisting of globular silica gel, inorganic porous materials such as unglazed plates, and resins such as ethylene-vinyl acetate copolymer, or the like.

The repellent agent can be mixed with a resin to be used as part of a dog's collar.

The amount of the repellent compound contained in the repellent agent of the present invention depends on the form of the repellent agent, the method of use and other conditions, but is generally from 0.1 to 90% by weight based on the repellent agent.

More specifically, the amount of the repellent compound is from 0.1 to 30% by weight in the case of a powder, from 0.1 to 90% by weight in the case of an emulsion, from 10 to 30% by weight in the case of a wettable powder, from 0.5 to 15% by weight in the case of granules, from 1 to 25% by weight in the case of a lotion, and from 0.1 to 20% by weight in the case of a cream.

The repellent agent against harmful insects according to the present invention can also be used in combination with herbicides and insecticides, plant growth regulators, fungicides, miticides, subliming insect proofers, known repellent agents against harmful insects, pigments, or stabilizers.

Further, a perfume composition according to the present invention can be produced preferably by mixing the repellent agent with perfumes or by mixing the repellent agent, perfumes with additives which are used conventionally. Such additives include hydrocarbons (paraffin, limonene, and the like), esters (diethylphthalate, benzylbenzoate and the like), alcohols (ethanol, isopropanol and the like) or ethers (dipropyleneglycol, diethyleneglycol, diethyleneglycol dimethyl ether and the like).

Most known perfumes can be used as a perfume. The amount of the perfume is not specifically limited, but is generally from about 0.001 to 30% by weight, preferably from about 0.1 to 20% by weight based on the entire perfume composition. In addition, the amount of the perfume is preferably from about 1 to 95% by weight based on the entire repellent composition. In the case of using a perfume in combination with an interior perfume composition having a repellent effect or the like, for example, the perfume can be used in an amount of from 1 to 95% by weight, preferably from about 5 to 60% by weight.

Since the above-mentioned compounds (1), (2), (3), (4), (5), and the like exhibit coolness-sensitivity, they can also be used as a coolness-sensitizer in addition to being used as a repellent agent. Further they can also be used as a humectant.

The present invention provides a repellent agent against hematophagous and biting insects including mosquitoes, horseflies, fleas, ticks, lice, and the like, which is superior in durability of repellent effect than the known repellent agents. The present invention also provides a perfume composition comprising at least one kind of a repellent agent, which has an excellent repellent effect against hematophagous and biting insects inclusive of mosquitoes, houseflies, fleas, ticks, lice, and the like.

Although the present invention is explained hereinafter with reference to the Examples and Test Examples, it is not limited thereto.

Apparatuses used in the Examples are as follows:

(1) Optical rotation: DIP-360, manufactured by Nippon Bunko Co.

(2) Infrared absorption: IR-810, manufactured by Nippon Bunko Co.

(3) Nuclear magnetic resonance (NMR): AMX-400, manufactured by Bruker Co.

(4) Mass spectrometry (MS): M-80, manufactured by Hitachi, Ltd.

Incidentally, part(s) means part(s) by weight, otherwise specified.

EXAMPLE 1

Synthesis of p-menth-8-ene-3,9-diol (1)

Into a four-mouth flask (volume: 100 ml) were added 1-n-isopulegol (13 g, 0.0844 mol), sodium carbonate (9.8 g, 0.928 mol), and toluene (20 ml), and the resultant mixture was cooled down to below 5° C. Into this solution was added dropwise 40% peracetic acid (17.6 g, 0.0928 mol) at a temperature of from 0° to 10° C. for 2 hours. Upon completion, the mixture was continuously stirred for reaction at a temperature below 10° C. for 3 hours, washed twice with brine, and concentrated.

The resultant oxidized concentrate was dissolved in tetrahydrofuran (hereinafter referred to as "THF") (30 ml), and the resultant solution was added dropwise into a solution of lithium diisopropylamide (0.25 mol) in THF (270 ml) which was cooled down to 0° C., while keeping the temperature below 5° C. Upon completion, the mixture was warmed and reacted at 45° C. for 1 hour, and then the mixture which cooled down to room temperature was poured onto ice water for separation. The THF layer was separated, washed with brine, dried, and concentrated to give a crude product (9.2 g). The crude product was recrystallized with ethyl acetate to give the title compound (1) (6.0 g) (Theoretical yield: 41.5%). Analytical results on the title compound are given below.

IR (NaCl, cm−1): 3600, 3100, 3000, 2950, 2900, 1660, 1450, 1300, 1230, 1130, 1100, 1060, 1050, 1010, 980, 910, 890

MS (20 eV, m/z): 170 (M+, 0.3), 152, 137, 124, 108, 98, 96, 94, 82, 68, 42

NMR (CDCl3, 400 mHz, ppm): 5.18 (1H, dt, J=1.2, 0.8), 5.02 (1H, d, J=1.0), 4.1 (1H, dd, J =12.8, 0.8), 4.06 (1H, dd, J=12.8, 0.8), 3.52 (1H, dt, J=4.2, 10.7), 3.1 (2H, br.s), 2.0 (1H, dm, J=12.4), 1.93 (1H, ddd, J=3.6, 10.7, 12), 1.72 (1H, dq, J=3.3, 13.2), 1.63 (1H, dm, J=10), 1.52 (1H, m), 1.35 (2H, dq, J=3.3, 12.8), 1.0 (H, dt, J=11, 12.2), 0.95 (3H, d, J=6.6), 0.92 (1H, dq, J=3.5, 13)

EXAMPLE 2

Synthesis of 9-hydroxymethyl-p-menthan-3-ol (2)

Into a four-mouthflask (volume: 100 ml) in which the inside was replaced by nitrogen were supplied diethyl ether (hereinafter referred to as "ether") and lithium aluminum hydride (0.2 g, 5.5 mmol). To this solution was added dropwise at room temperature an ether solution of 5,9-dimethyl-2-oxabicyclo-[4,4,0]-decan-3-one (0.1 g, 0.55 mmol) which had been separately prepared. The mixture was allowed to react at the same temperature for 1 hour, and the reaction solution was poured into a 10% aqueous hydrochloric acid solution for separation. The ether layer was separated, washed with brine, dried over anhydrous magnesium sulfate and concentrated. The resultant crude product was purified by column chromatography on silica gel to give the title compound (2) (80 mg) (Theoretical yield: 78.1%). Analytical results on the title compound are given below.

IR (NaCl, cm−1): 3600–3100, 2950, 2920, 2850, 1460, 1380, 1100, 1040, 1000, 970, 850)

MS (20 eV, m/z): 186 (M+, 1), 150, 135, 124, 112, 95, 81, 71, 55, 43, 18

NMR (CDCl3, 40 mHz, ppm): 0.82 (3H, d, J=6.9), 0.91 (3H, d, J=6.6), 1.24 (2H, m), 1.42 (1H, m), 1.52 (2H, q, J=6.6, 7.1), 1.66 (2H, m), 1.85 (1H, br.s), 1.97 (1H, m), 2.20 (2H, m), 2.48 (1H, br.s), 2.68 (1H, br.s), 3.45 (1H, m), 3.68 (2H, m)

EXAMPLE 3

Synthesis of 3-(2-hydroxyethyl)-p-menthan-8-ol (3)

Into a four-mouth flask (volume: 100 ml), in which the inside was substituted by nitrogen, were supplied ether and lithium aluminum hydride (1.9 g; 51 mmol). To this mixture was added dropwise at room temperature an ether solution of 2,2,8-trimethyl-3-oxabicyclo-[4,4,0]- decan-4-one (1 g; 5.1 mmol) which had been separately prepared. The resultant mixture was allowed to react at the same temperature for 1 hour, and the reaction solution was poured into a 10% aqueous solution of hydrochloric acid for separation. The ether layer was separated, washed with brine, dried over anhydrous magnesium sulfate, and concentrated. The resultant crude product was purified by column chromatography on silica gel to give the title compound (3) (0.9 g; 4.5 mmol) (Theoretical yield: 88.2%). Analytical results on the title compound are given below.

IR (NaCl, cm−1): 3100–3600, 2950, 2900, 1460, 1380, 1200, 1060, 1050, 1020, 970, 950, 910, 880

MS( 20 eV, m/z): 182 (M+-18), 164, 138, 124, 108, 90, 84, 79, 70

NMR (400 mHz, CDCl, ppm): 0.88 (3H, d, J=6.5), 0.93 (2H, m), 1,18 (3H, s), 1.23 (3H, s), 1–34 (2H, m), 1.58 (2H, m), 1.70 (2H, m), 1.79 (2H, m), 2.09 (1H, m), 2.22 (1H, br.s), 2.75 (1H, br.s), 3.69 (1H, m), 3.81 (1H, m)

EXAMPLE 4

Synthesis of p-menthan-3,8,9-triol (4)

Into a solution of acetone (116 g; 2 mol) and a 3% aqueous solution of sulfuric acid (35 g) was added 8,9-epoxy-p-menthan-3-ol (17 g; 0.1 mol), and the mixture was stirred at room temperature for 16 hours. Then, the acetone was distilled and recovered, and the concentrated solution was mixed with water (40 ml) and heated to within 80° C. of the distilling temperature to completely recover the acetone. The remaining aqueous solution was cooled, neutralized with a 10% aqueous solution of sodium carbonate, and saturated with sodium chloride. The reaction product was extracted with THF, dried over anhydrous magnesium sulfate, and concentrated to give a crude product (19 g). The crude product was purified by column chromatography on silica gel. That is, the crude product was eluted with 50% ethyl acetate-n-hexane, then eluted with ethyl acetate only, and the eluate was concentrated to give a highly pure title compound (4) (7 g; a mixture of diastereomers). This was a mixture of solid and liquid, and the mixing ratio of diastereomers was calculated as 7:3 by measuring with NMR. Analytical results on the title compound are given below. Optical rotation [α]D25=+15.6 (c=1, EtOH)

IR (KBr tabret, cm1): 6670, 1465, 1455, 1380, 1360, 1270, 1240, 1195, 1150, 1105, 1085, 1060, 1050, 1030, 1005, 975, 940, 930, 910, 9880, 850

MS (20 eV, m/z): 188 (0), 157, 139, 123, 121, 109, 108, 96, 95, 87, 75, 55, 54, 43, 28

NMR (400 mHz, CDCl3, ppm): 0.86–0.94 (m), 0.915 (d, J=6.6), 0.92 (d, J=6.6), 0.94–1.08 (m), 1.14 (s) 1.18 (s), 1.43 (m), 1.51 (m), 1.6–1.7 (m), 1.72–1.79 (m), 1.88–1.98 (m), 3.04 (t), 3.19 (t) 3.35 (dd), 3.43 (dd), 3.51 (dd), 3.73 (dd), 3.8 (dt), 4.1 (s), 4.29 (s), 4.76 (s)

The above-mentioned solid was filtered and recrystallized with diisopropyl ether to give short crystals having a melting point of 72° to 72.5° C. This was confirmed as 8S. The NMR spectrum of 8S was given below:

NMR (40 mHz, CDCl3, ppm):

0.86–0.94 (1H, m), 0.915 (3H, d, J=6.6), 0.96–1.07 (2H, m), 1.17 (3H, s), 1.43 (1H, m), 1.51 (1H, m), 1.6–1.7 (1H, m), 1.72–1.79 (1H, m), 1.88–1.94 (1H, m), 3.43 (1H, s), 3.44 (1H, d, J=11.1), 3.72 (1H, d, J=11.1), 3.77 (1H, dt, J=4.2, 10.4), 4.45 (1H, s), 4.82 (1H, s)

EXAMPLE 5

Synthesis of 9-methoxy-p-menthan-3,8-diol (5)

Into a solution of a 28% sodium methylate-methanol solution (19.2 g; 0.1mol) in methanol (22ml) was added dropwise a solution of 8,9-epoxy-p-menthan-2-ol (17 g; 0.1 mol) in methanol (10 ml) with heating under reflux for over one hour. Upon completion, the resultant mixture was stirred at the same temperature for 3 hours for reaction. After cooling, glacial acetic acid (6.6 g; 0.11 mol) was added dropwise to the mixture for neutralizing the alkali. The oil layer which had been separated by adding chilled water was extracted with toluene, washed with brine until neutral, dried over anhydrous magnesium sulfate and concentrated under a low vacuum while recovering the toluene to give a crude product (17 g). The crude product was distilled under a high vacuum at a boiling point of 114° to 150° C./0.9 mm Hg to give the title compound (5) (15.2 g) (Theoretical yield: 75%). Analytical results on the title compound are given below.

Purity: 99.3% (by gas chromatography). Diastereomer ratio: 45.4:54.5. Optical rotation [(α]D25=−10.8 (c=1, EtOH)

IR (NaCl, cm−1): 3320, 1195, 1180, 1150, 1120, 1110, 1055, 1030, 1005, 980, 970, 910, 880, 850

MS (20 eV, m/e): M+=202 (0), 157, 139, 95, 89, 81, 71, 67, 57, 55, 43, 41

MNR (400 mHz, CDCl3, ppm): 0.72–1.0 (m), 0.83 (d, J=6.6), 0.84 (d, J=6.6), 1.09 (s), 1.14 (s), 1.28–1.43 (m), 1.48–1.60 (m), 1.63–1.69 (m), $_{1.83-1.91}$ (m), 3.09 (d, J=9.4), 3.28 (d, J=9.4), 3.29 (d, J=9.4), 3.31 (s), 3.33 (s), 3.41 (d, J=9.4), 3.62–3.69 (m), 3.86 (s), 4.03 (s), 4.64 (d, J=2.4), 4.76 (d, J=1.6)

EXAMPLE 6

Synthesis of 9-ethoxy-p-menthan-3,8-diol

To a solution of sodium ethylate (6.8 g; 0.1 mol) in ethanol (57 ml) was added dropwise a solution of 8,9-epoxy-p-menthan-3-ol (17 g; 0.1 mol) in ethanol (10ml) with heating under reflux for over one hour. Upon completion, the mixture was stirred at the same temperature for 2 hours for reaction. After cooling, glacial acetic acid (6.6 g; 0.11 mol) was dropwise added to neutralize the alkali. The oil layer which had been separated by adding chilled water was extracted with toluene, washed with brine until neutral, dried over anhydrous magnesium sulfate and concentrated under a low vacuum while recovering the toluene to give a crude product (19.5 g). The crude product was distilled under a high vacuum at a boiling point of 113° to 114° C./0.6 mm Hg to give the purified title product (15 g) (Theoretical yield: 69.4%). Analytical results on the title compound are given below.

Purity: 98.2% (by gas chromatography). Diastereomer ratio: 47.5:52.5. Optical rotation [α]D25=−11.0 (c=1, EtOH)

IR (NaCl, cm-1): 3325, 1220, 1150, 1120, 1055, 1030, 105, 980, 910, 880, 850

MS (20 eV, m/z): M+=202 (0), 183, 157, 139, 103, 95, 81, 75, 71, 59, 43

MNR (400 mHz, CDCl3, ppm): 0.915 (d, J=6.6), 0.92 (d, J=6.6), 0.82–1.07 (m), 1.18 (s), 1.209 (d, J=7), 1.215 (t, J=7), 1.23 (s), 1.36–1.47 (m), 1.47–1.76 (m), 1.92–2.0 (m), 3.19 (d, J=9.1), 3.36 (d, J=9.1), 3.40 (d, J=9.1), 3.41 (s), 3.49–3.58 (m), 3.68–3.76 (m), 4.58 (d, J=0.18), 4.75 (d, J=0.8)

EXAMPLE 7

Compound (3) (10 parts) prepared in Example 3 was dissolved in a mixed solution (1:1) (60 parts) of tetralin and methylnaphthalene.

To this solution was added a mixture (8:2) (30 parts) of nonylphenyl-ethylene oxide condensate and calcium dodecylbenzenesulfonate, to obtain an emulsion.

The emulsion was diluted with water to 10 to 100 times of consistency and used as a sprinkling agent or coating agent.

EXAMPLE 8

Compound (2) (1 part) prepared in Example 2 was mixed with cetyl alcohol (2 parts).

To this mixture was added lanolin (1 part), stearic acid (12 parts), palmitic acid (1 part) and water (67 parts), and the resultant mixture was dissolved and mixed with heating. Hot glycerin (14 parts) was poured thereonto and the mixture was stirred sufficiently to give a cream.

This emulsion is used by itself for application to a human or animal body.

EXAMPLE 9

A mixture of lanolin (1 part), stearic acid (7 parts) and polyoxyethylene sorbitan monostearate (7 parts) was heated at 75° C., added to a mixture (60° C.) of water (82 parts) and salicylic acid (2 parts), and further mixed with Compound (1) (1 part) with stirring to give a lotion.

This lotion is used by itself for application to a human or animal body.

EXAMPLE 10

Compound (3) (2 parts) prepared in Example 3 and Compound (4) (3 parts) prepared in Example 4 were dissolved in methyl cellosolve (15 parts). The solution was mixed with liquidified petroleum (80 parts) to give a uniform solution, and thus a raw material for an aerosol was obtained.

EXAMPLE 11

To a mixture of Compound (2) (1 part) prepared in Example 2 and Compound (5) (1 part) prepared in Example 5 were added a mixture (96 parts; 1:2 weight ratio) of calcium carbonate and talc, and the resultant mixture was pulverized to give a sufficiently uniform dispersion.

Further, anhydrous silicic acid (2 parts) was added and the mixture pulverized to give powders.

These powders are used by themselves by sprinkling.

TEST EXAMPLE

Test Example for repellent effect: Test for repellent potency against blood-sucking in mice Test insect: Culex pipiens pallens, Numadzu colony, 19–22 days age after eclosion, female imagoes.

Test method: A mouse (male, body weight: about 40 g) was fixed on the ceiling of a metallic net cage of 40 mesh (12.5 cm long×6 cm wide, surface area: 150 cm$^2$) so as not to move about. Over the surface of the metallic net cage was uniformly and dropwise added 1.5 ml (equivalent to 1 ml/100 cm$^2$) of a sample (a repellent composition or the like) with a pipet. After drying for one hour, 25 test imagoes were released into the metallic net cage.

Hematophagous ratio was calculated from the number of mosquitoes which sucked blood (the mosquitoes which sucked blood were recognized visually because of blood pooling in the belly).

The test was performed in two runs, and the repellent index was calculated from the obtained result according to the following formula (Formula 6). Then, the repellent effect was judged.

$$\text{Repellent index} = \left(1 - \frac{\text{Hematophagous ratio in treated section}}{\text{Hematophagous ration in control section}}\right) \times 100$$

Repellent index was defined as 100 when a complete repellent result was observed, and was defined as 0 when the hematophagous ratio was the same as in the control. Environmental conditions in the test room were as follows:

Room temperature: 25°–26° C.

Relative humidity: 60–75%

Lighting: Complete darkness

Table 1 shows the result in terms of the hematophagous ratio.

TABLE 1

| No. | Sample* | Hematophagous ratio (%) at the time lapsed (hrs.) | | | | | | |
|---|---|---|---|---|---|---|---|---|
| | | 2 | 4 | 6 | 8 | 10 | 12 | 24 hrs. |
| 1 | 1 | 0 | 0 | 0 | 2 | 6.0 | 10.0 | 14.0 |
| 2 | 2 | 0 | 0 | 0 | 0 | 4.0 | 6.0 | 12.0 |
| 3 | 3 | 0 | 0 | 0 | 0 | 4.0 | 4.0 | 4.0 |
| 4 | 3 + 4 | 0 | 0 | 0 | 0 | 0 | 2.0 | 4.0 |
| 5 | 2 + 5 | 0 | 0 | 0 | 0 | 2.0 | 5.0 | 10.0 |
| 6 | A | 0 | 0 | 0 | 3.1 | 12.3 | 24.4 | 65.7 |
| 7 | B | 0 | 1.3 | 14.7 | 24.1 | 44.0 | 58.2 | 69.9 |
| | Control section | 14.0 | 18.0 | 20.0 | 24.0 | 44.0 | 58.0 | 70.0 |

*As samples, five kinds of one or a mixture of the repellent compounds (1–5) prepared in the Examples and known repellent compounds (A: 1-p-menthan-3,8-diol and B: N,N-diethyl-m-toluamide) were prepared according to the following formulation:

Formulation of the samples:

99% Ethanol: 90% by weight

Water: 9% by weight

Repellent compound: 1% by weight

Compound 1: Compound prepared in Example 1

Compound 2: Compound prepared in Example 2

Compound 3: Compound prepared in Example 3

Compound 4: Compound prepared in Example 4

Compound 5: Compound prepared in Example 5

Further, a mixture of Compound 3 and Compound 4 (2:3 ratio by weight) was used in Test No. 4, and a mixture of Compound 2 and Compound 5 (1:1 ratio by weight) was used in Test No. 5.

Table 2 shows the repellent index which was calculated according to the results.

TABLE 2

| No. | Sample* | Repellent index at the time elapsed | | | | | | |
|---|---|---|---|---|---|---|---|---|
| | | 2 | 4 | 6 | 8 | 10 | 12 | 24 hrs. |
| 1 | 1 | 100 | 100 | 100 | 91.7 | 86.4 | 82.8 | 80.0 |
| 2 | 2 | 100 | 100 | 100 | 100 | 90.9 | 89.7 | 82.9 |
| 3 | 3 | 100 | 100 | 100 | 100 | 90.9 | 93.1 | 94.3 |
| 4 | 3 + 4 | 100 | 100 | 100 | 100 | 100 | 96.6 | 94.3 |
| 5 | 2 + 5 | 100 | 100 | 100 | 100 | 95.4 | 91.4 | 85.8 |
| 6 | A | 100 | 100 | 100 | 87 | 72.4 | 56.8 | 6.1 |
| 7 | B | 100 | 93 | 26.5 | 0 | 0 | 0 | 0 |

As can be clearly understood from the above results, the repellent agents according to the present invention have been shown to have particularly excellent durability as compared to the known repellent agents. Specifically, the known repellent agents showed a hematophagous ratio of 6.1% and 0% after 24 hours, while the repellent agents according to the present invention showed a hematophagous ratio of 80% or more in all cases.

EXAMPLE 12

Indoor perfume agents having a flower fragrance like lavender for the purpose of repelling harmful insects were produced according to the following formulation (Table 3).

TABLE 3

| Composition | Parts by weight |
|---|---|
| Coumarin | 0.5 |
| n-Decyl aldehyde | 0.01 |
| Geraniol | 4.0 |
| 1,8-Cineole | 2.0 |
| 3-Octanol | 0.4 |
| n-Hexyl butyrate | 0.5 |
| α-Pinene | 3.0 |
| L-Citronellol | 5.0 |
| Geranyl acetate | 0.4 |
| Linalyl acetate | 9.0 |
| Linalool | 6.0 |
| Nerol | 2.0 |
| Nopil acetate | 3.0 |
| Terpineol | 5.0 |
| Terpinyl acetate | 12.0 |
| Lavandine oil | 25.0 |

TABLE 3-continued

| Composition | Parts by weight |
|---|---|
| Dipropylene glycol | 11.69 |
| Compound of Example 1 | 10.5 |
| Total | 100.00 |

EXAMPLE 13

A fragrance for high-taste body lotion containing lemon-like citrus perfume for the purpose of repelling harmful insects was produced according to the following formulation (Table 4).

TABLE 4

| Composition | Parts by weight |
|---|---|
| n-Octyl aldehyde | 0.1 |
| n-Nonyl aldehyde | 1.2 |
| n-Decyl aldehyde | 2.2 |
| n-Undecyl aldehyde | 1.8 |
| n-Dodecyl aldehyde | 0.1 |
| Citral | 6.0 |
| 1-Citronellal | 2.0 |
| 1-Citronellol | 3.6 |
| 1-Rose oxide | 0.5 |
| Ethyl n-butyrate | 0.5 |
| Cis-3-hexenol | 0.2 |
| Geraniol | 0.3 |
| Linalool | 3.0 |
| Linalyl acetate | 4.5 |
| Grape fruit oil | 5.0 |
| Lime oil | 4.0 |
| Orange oil | 5.0 |
| Terpen oil | 10.0 |
| Lemon oil | 35.0 |
| Compound of Example 2 | 15.0 |
| Total | 100.00 |

Although the present invention has been described in conjunction with certain preferred embodiments, it is not limited thereto but instead includes all embodiments within the literal and equitable scope of the appended claims.

What is claimed is:

1. The compound, 9-hydroxymethyl-p-methan-3-ol.
2. The compound, 3-(3-hydroxyethyl)-p-menthan-8-ol.

* * * * *